US00PP11046P

United States Patent [19]

Zary

[11] Patent Number: Plant 11,046

[45] Date of Patent: Aug. 31, 1999

[54] HYBRID TEA ROSE PLANT NAMED 'JACSASH'

[75] Inventor: Keith W. Zary, Thousand Oaks, Calif.

[73] Assignee: Bear Creek Gardens, Inc., Medford, Oreg.

[21] Appl. No.: 09/028,856

[22] Filed: Feb. 24, 1998

[51] Int. Cl.[6] ..... A01H 5/00

[52] U.S. Cl. ..... Plt./138

[58] Field of Search ..... Plt./137, 138, 139

[56] References Cited

U.S. PATENT DOCUMENTS

P.P. 4,284 7/1978 Lindquist, Sr. ..... Plt./138

*Primary Examiner*—Howard J. Locker

*Attorney, Agent, or Firm*—Klarquist Sparkman Campbell Leigh & Whinston, LLP

[57] ABSTRACT

Hybrid tea rose plant having large flowers, well filled with petals of heavy substance and having a strong, sweet fragrance; strong, upright growth; large, glossy, dark green foliage; and resistance to common fungal diseases.

1 Drawing Sheet

The present invention relates to a new and distinct variety of rose plant of the hybrid tea class which was originated by me by crossing the variety 'Fragrant Cloud,' U.S. Plant Pat. No. 2,574, with the variety 'POULman,' U.S. Plant Pat. No. 6,264.

The primary objective of this breeding was to produce a new rose variety having the strong fragrance and upright growth of the female parent combined with the dark green, glossy foliage, disease resistance, large flowers, and heavy petal substance of the male parent. The objective was substantially achieved, along with other desirable improvements, as evidenced by the following unique combination of characteristics that are outstanding in the new variety and that distinguish it from its parents, as well as from all other varieties of which I am aware:

1. Strong, sweet fragrance;
2. Large flowers, well filled with petals of heavy substance;
3. Strong, upright growth;
4. Large, glossy, dark green foliage;
5. Resistance to common fungal diseases.

The large flowers open fully but do not show their reproductive parts. The center of the flower remains filled with petals giving it an "old rose" look.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Fragrant Cloud', U.S. Plant Pat. No. 2,574.

*Pollen parent.*—'POULman', U.S. Plant Pat. No. 6,264.

Classification:

*Botanical.*—Rosa hybrida.

*Commercial.*—Hybrid tea.

Flower

Observations made from specimens grown in a garden environment at Somis, Calif., from January 1996 to December 1997.

Blooming habit: Recurrent.

Bud:

*Size.*—2" long when the petals start to unfurl.

*Form.*—Long, pointed ovoid.

*Color.*—When sepals first divide, bud color is Red Group 46B. When half blown, the upper sides of the petals are Red Group 46D, the lower sides of the petals are Red Group 46C.

*Sepals.*—Color: Green Group 138B. Surface texture: Covered in fine hairs. There are three normally to heavily appendaged sepals. There are two unappendaged sepals with hairy edges.

*Receptacle.*—Color: Yellow-Green Group 146B. Shape: Funnel. Size: Medium (7/16"×5/16"). Surface: Smooth.

*Peduncle.*—Length: Medium (3½"). Surface: Smooth. Color: Medium green. Strength: Stiff, erect.

Bloom:

*Size.*—Large. Average open size is 5".

*Borne.*—Singly.

*Stems.*—Medium (16–18"), strong.

*Form.*—When first open: High centered. Permanence: Retains its form to the end, outer petals curl back.

*Petalage.*—Number of petals under normal conditions: 40–45.

*Color.*—The upper sides of the petals are Red Group 46D. The reverse sides of the petals are Red Group 46C. The base of each petal has a small (3/16"×3/16") whitish half moon at the point of attachment. The major color on the upper sides is Red Group 46D.

*Variegations.*—Occasional whitish streak on the guard petals.

*Discoloration.*—At the end of the first day: No change. At the end of the third day: No change. In very old flowers (seven to eight days old on the plant), there is a general fading to near Red Group 54C on the upper surface and to near Red Group 54B on the lower surface of the petal.

*Fragrance.*—Strong.

Petals:

*Texture.*—Thick.

*Shape.*—Round on the outer petals, deltoid toward the center of the flower.

*Form.*—Tips slightly recurved, edges slightly quilled.

*Arrangement.*—Imbricated. Petaloids in the center: Few.

*Persistence.*—Petals drop off cleanly before drying.

*Lastingness.*—On the plant: Long (7–8 days). As a cut flower: Long (9–10 days).

Reproductive parts:

*Anthers.*—Size: Medium. Quantity: Many. Color: Yellow. Arrangement: Regular around styles mixed with occasional petaloids.

*Filaments.*—Color: Yellow.

*Pollen.*—Color: Gold yellow.

*Styles.*—Color: Red.

*Stigmas.*—Color: Greenish white.

Plant:

*Form.*—Bush.

*Growth.*—Vigorous; upright; branching. At maturity, height is five and one-half feet, width is four feet.

Foliage:

*Number of leaflets on normal mid-stem leaves.*—Five.

*Size.*—Large (6"×6½").

*Quantity.*—Abundant.

*Color.*—New foliage: Upper and lower sides: Greyed-Red Group 178A. Old foliage: Upper side: Green Group 135A. Lower side: Green Group 139C.

Leaflets:

*Shape.*—Pointed oval.

*Texture.*—Upper side: Leathery, glossy.

*Edge.*—Serrated.

*Serration.*—Single, small.

*Petiole rachis.*—Color: Yellow-Green Group 147C when mature, reddish when young but fully expanded.

*Petiole underside.*—Smooth.

*Stipules.*—Long (⅗"), serrated.

*Disease resistance.*—Resistant to mildew and rust under normal growing conditions at Somis, Calif.

Wood:

*New wood.*—Color: Greyed-Red Group 178A. Bark: Smooth.

*Old wood.*—Color: Green Group 137D. Bark: Smooth.

Prickles:

*Quantity.*—On main canes from base: Ordinary. On laterals from main canes: Ordinary.

*Form.*—Medium, hooked downward.

*Color when young.*—Red Group 46A.

Small prickles:

*Quantity.*—On main stalks: None. On laterals: None.

I claim:

1. A new and distinct variety of rose plant of the hybrid tea class, as herein shown and described, characterized particularly by large flowers, well filled with petals of heavy substance and having a strong, sweet fragrance; strong, upright growth; large, glossy, dark green foliage; and resistance to common fungal diseases.

* * * * *

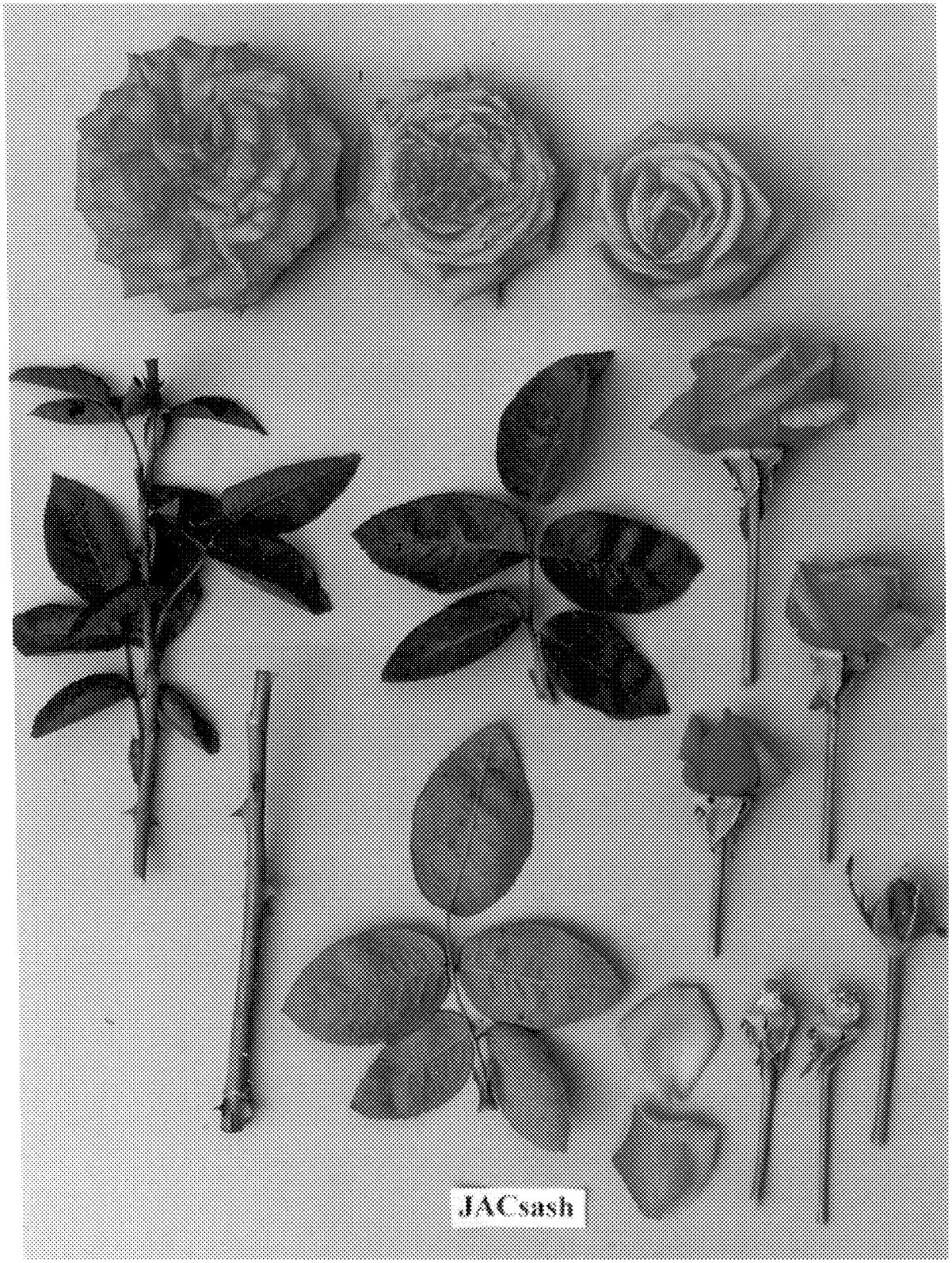
JACsash